(12) United States Patent
Eder (10) Patent No.: US 8,372,056 B2
(45) Date of Patent: Feb. 12, 2013

(54) HYBRID MICRO GUIDE CATHETER

(75) Inventor: Joseph C. Eder, Los Altos Hills, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/025,381

(22) Filed: Feb. 11, 2011

(65) Prior Publication Data

US 2011/0137163 A1 Jun. 9, 2011

Related U.S. Application Data

(63) Continuation of application No. 10/827,565, filed on Apr. 19, 2004, now Pat. No. 7,887,529.

(51) Int. Cl.
*A61M 25/00* (2006.01)
(52) U.S. Cl. .......................... 604/523; 604/43
(58) Field of Classification Search .................. 604/523, 604/264, 43
See application file for complete search history.

(56) References Cited

U.S. PATENT DOCUMENTS

| | | | |
|---|---|---|---|
| 4,299,226 A | 11/1981 | Banka | |
| 5,328,469 A | 7/1994 | Coletti | |
| 5,368,567 A | 11/1994 | Lee | |
| 5,374,245 A | 12/1994 | Mahurkar | |
| 5,380,282 A | 1/1995 | Burns | |
| 5,385,562 A | 1/1995 | Adams et al. | |
| 5,409,455 A | 4/1995 | Belden | |
| 5,451,233 A | 9/1995 | Yock | |
| 5,496,275 A | 3/1996 | Sirhan et al. | |
| 5,501,668 A | 3/1996 | Kontos | |
| 5,554,118 A | 9/1996 | Jang | |
| 5,558,644 A | 9/1996 | Boyd et al. | |
| 5,569,196 A | 10/1996 | Muni et al. | |
| 5,728,067 A | 3/1998 | Enger | |
| 5,746,717 A | 5/1998 | Aigner | |
| 5,772,609 A | 6/1998 | Nguyen et al. | |
| 5,820,585 A | 10/1998 | Mobin-Uddin et al. | |
| 5,858,009 A | 1/1999 | Jonkman | |
| 5,876,375 A | 3/1999 | Penny | |
| 5,882,336 A | 3/1999 | Janacek | |
| 6,007,530 A | 12/1999 | Dornhofer et al. | |
| 6,022,336 A | 2/2000 | Zadno-Azizi et al. | |
| 6,033,381 A | 3/2000 | Kontos | |
| 6,036,715 A | 3/2000 | Yock | |
| RE36,857 E | 9/2000 | Euteneuer et al. | |
| 6,139,510 A | 10/2000 | Palermo | |
| 6,146,373 A * | 11/2000 | Cragg et al. | 604/523 |
| 6,159,195 A | 12/2000 | Ha et al. | |
| 6,165,197 A | 12/2000 | Yock | |
| 6,428,489 B1 | 8/2002 | Jacobsen et al. | |

(Continued)

FOREIGN PATENT DOCUMENTS

DE 31 30 454 4/1983
EP 1 374 941 1/2004

(Continued)

*Primary Examiner* — Laura Bouchelle
(74) *Attorney, Agent, or Firm* — Seager, Tufte & Wickhem, LLC (57) ABSTRACT

A hybrid microguide catheter and method for making and using the same. The catheter may include a first tubular member and a second tubular member. The tubular members may be arranged so that the second tubular member extends distally beyond the first tubular member. Alternatively, the catheter may include a tubular body having a first opening and a second opening. The first opening may be positioned along the tubular body a distance from the second opening.

12 Claims, 5 Drawing Sheets

U.S. PATENT DOCUMENTS

| | | |
|---|---|---|
| 6,575,993 B1 * | 6/2003 | Yock .............................. 606/194 |
| 6,579,246 B2 | 6/2003 | Jacobsen et al. |
| 6,695,832 B2 * | 2/2004 | Schon et al. ................... 604/544 |
| 6,733,473 B1 | 5/2004 | Reifart et al. |
| 2003/0093059 A1 | 5/2003 | Griffin et al. |
| 2003/0130577 A1 | 7/2003 | Purdy et al. |
| 2003/0163082 A1 | 8/2003 | Mertens |
| 2004/0039331 A1 | 2/2004 | Coppi et al. |
| 2004/0193140 A1 | 9/2004 | Griffin et al. |

FOREIGN PATENT DOCUMENTS

| | | |
|---|---|---|
| WO | 97/29800 | 8/1997 |

* cited by examiner

HYBRID MICRO GUIDE CATHETER

RELATED APPLICATIONS

This application is a continuation of co-pending U.S. application Ser. No. 10/827,565, filed Apr. 19, 2004, the entire disclosure of which is incorporated herein by reference.

FIELD OF THE INVENTION

The present invention pertains to medical devices including catheters. More particularly, the present invention pertains to intravascular catheters with a support and visualization portion and a distal access portion.

BACKGROUND OF THE INVENTION

A wide variety of devices have been developed for medical use, for example, intravascular use. Some of these devices include guidewires, catheters, and other such devices that each have certain features and characteristics. Among the known medical devices, each has certain advantages and disadvantages. There is an ongoing need to provide alternative designs and methods for making and using medical devices with desirable characteristics and features.

SUMMARY OF THE INVENTION

The invention provides design, material, and manufacturing method alternatives for medical devices, for example, catheters. In at least some embodiments, the catheters include a support and visualization portion and a distal access portion. The support and visualization portion may be disposed near the proximal end region of the catheter and the distal access portion may be disposed near the distal end region of the catheter. These and some of the other features and characteristics of example embodiments are described in more detail below.

DETAILED DESCRIPTION

The following description should be read with reference to the drawings wherein like reference numerals indicate like elements throughout the several views. The detailed description and drawings illustrate example embodiments of the claimed invention.

Figure 1:
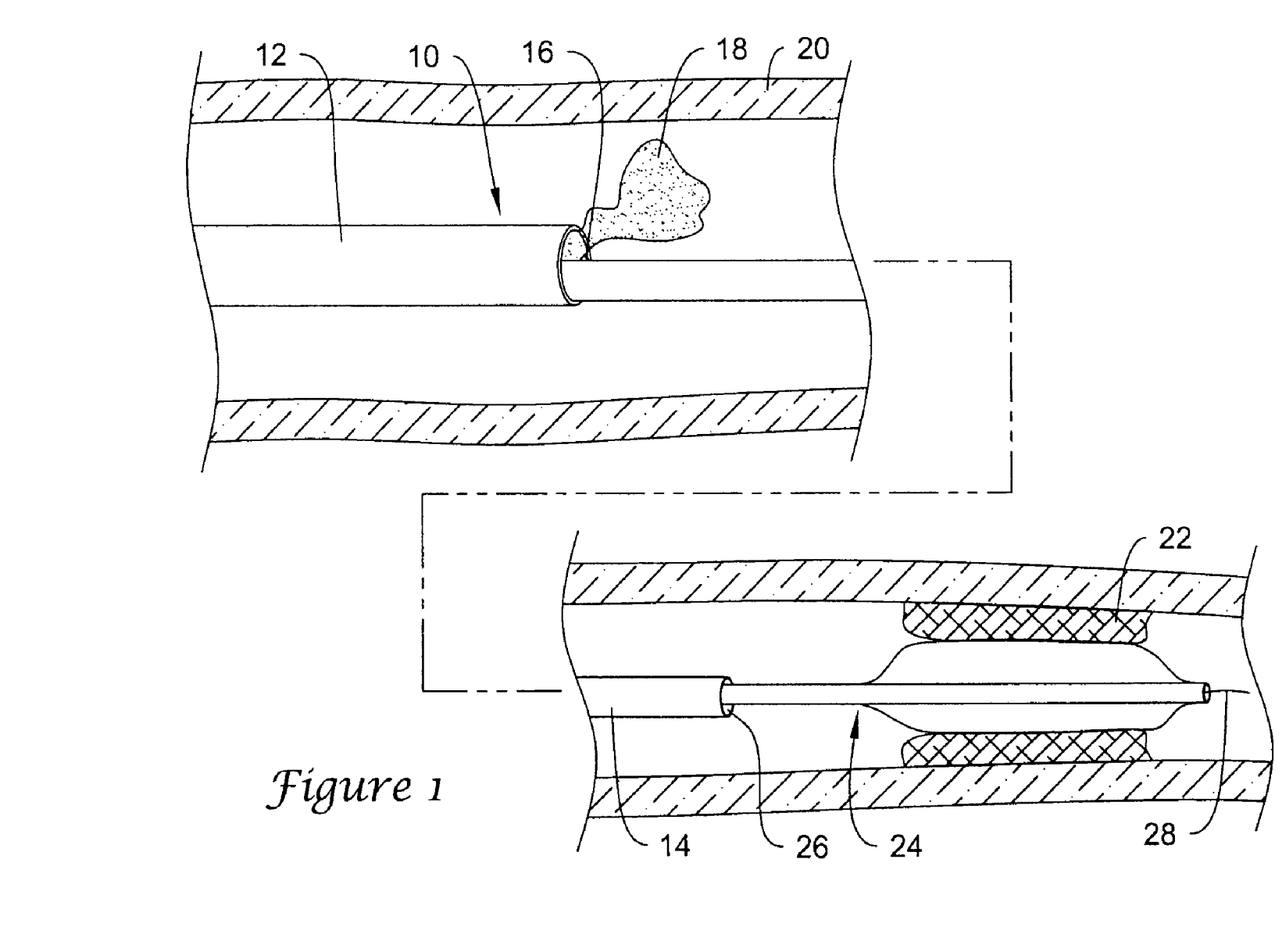
FIG. 1 is partial cross-sectional side view of an example catheter disposed in the blood vessel.

FIG. 1 is partial cross-sectional side view of an example catheter 10. Catheter 10 may include a proximal region 12 and a distal region 14. In at least some embodiments, proximal region 12 is adapted and configured so that it provides catheter 10 with a desirable amount of proximal stiffness. In addition, proximal region 12 may be used to enhance catheter visualization. For example, proximal region 12 may include a lumen 16 (better seen in FIG. 2) that can be used to infuse contrast media 18 (as a part of a standard fluoroscopy technique) into a blood vessel 20. Of course, other substances can be passed through lumen 16 as desired, including pharmacological agents.

In at least some embodiments, distal region 14 is adapted and configured so that it provides catheter 10 with distal access to target vascular regions. For example, distal region 14 may extend deeper within blood vessel 20 (which is, for example, exemplified by the narrowing of blood vessel 20 in the lower half of FIG. 1) to an area near an intravascular lesion 22. Once positioned, a microcatheter 24 may be passed through a lumen 26 defined in distal region 14. Microcatheter 24 may be any of a number of different known microcatheters such as guide catheters, balloon catheters, cutting balloon catheters, atherectomy catheters, stent delivery catheters, filter delivery catheters, and the like, or any other suitable medical device. Advancing microcatheter 24 through lumen 26 may include advancing microcatheter 24 over a guidewire 28 in the manner typically used in the art. Guidewire 28 may be similar to typical guidewires used in the art.

Figure 2:
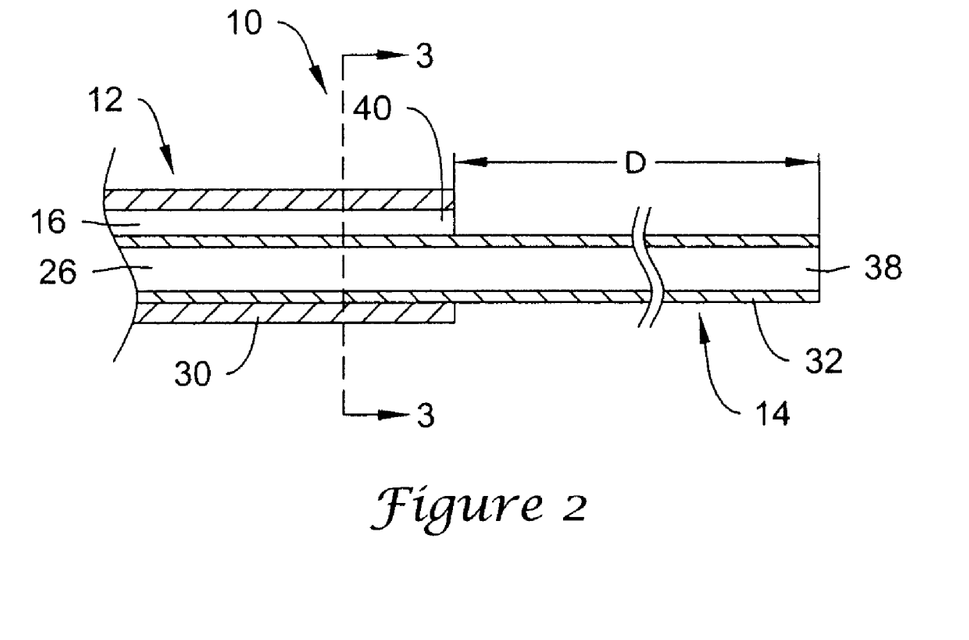
FIG. 2 is a cross-sectional view of the catheter shown in FIG. 1.

Catheter 10 may include a first tubular member 30 and a second tubular member 32 as illustrated in FIG. 2. According to this embodiment, the combination of first tubular member 30 and second tubular member 32 may define proximal region 12. A portion of second tubular member 32 may extend distally a distance D from first tubular member 30 in order to define distal region 12. Distance D may reflect the distance between a first opening 40 (through which, for example, contrast media or other substances can be infused) of first tubular member 30 and a second opening 38 (through which, for example, a microcatheter can be advanced) of second tubular member 32. In some embodiments, the length of distance D may be in the range about 1 to about 50 centimeters. In other embodiments, the length of distance D may be in the range about 10 to about 40 centimeters. In still other embodiments, the length of distance D may be in the range about 20 to about 40 centimeters. It should be noted that the form and arrangement of tubular members 30/32 need not be exactly as stated, because a number of other arrangements are contemplated. For example, second tubular member 32 need not be disposed as illustrated at proximal region 12, as it may be positioned anywhere in lumen 16.

Tubular members 30/32 may be made from any suitable material such as metals, metal alloys, metal-polymer composites, polymers, and the like or any other suitable material. In some embodiments, tubular members 30/32 have the same or similar material composition. In other embodiments, tubular members 30/32 have different material compositions. Below are some lists of materials that can be used to manufacture tubular members 30/32. The lists are not intended to be exhaustive or to be limiting. Some examples of suitable metals and metal alloys include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene (PE), Marlex high-density polyethylene, Marlex low-density polyethylene, linear low density polyethylene (for example, REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, tubular members 30/32 can be blended with a liquid crystal polymer (LCP). For example, the mixture can contain up to about 5% LCP. This has been found to enhance torqueability.

In some embodiments, a coating, for example, a lubricious, a hydrophilic, a protective, or other type of coating may be applied over portions or all of tubular members 30/32, or other portions of catheter 10. Hydrophobic coatings such as fluoropolymers provide a dry lubricity which improves catheter handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

In some embodiments, first tubular member 30 and/or second tubular member 32 may include one or more cuts or grooves formed therein (e.g., by micro-machining). Micro-machining tubular members 30/32 may be desirable because it allows a stiffer starting material (e.g., stainless steel, nickel-titanium alloy, etc.) to be used in the manufacturing of tubular members 30/32 that can be smaller, thinner, or otherwise have a lower profile than less stiff materials. This stiff material can then be micro-machined in order to impart the desired level of flexibility. Further discussion on the use of forming cuts, slots, or grooves as well micro-machining can be found in U.S. Patent Publication No. 2004/0193140, in U.S. Pat. No. 6,428,489, and in U.S. Patent Publication No. 2002/0013540, the entire disclosures of which are herein incorporated by reference.

Figures 3, 4, 5:
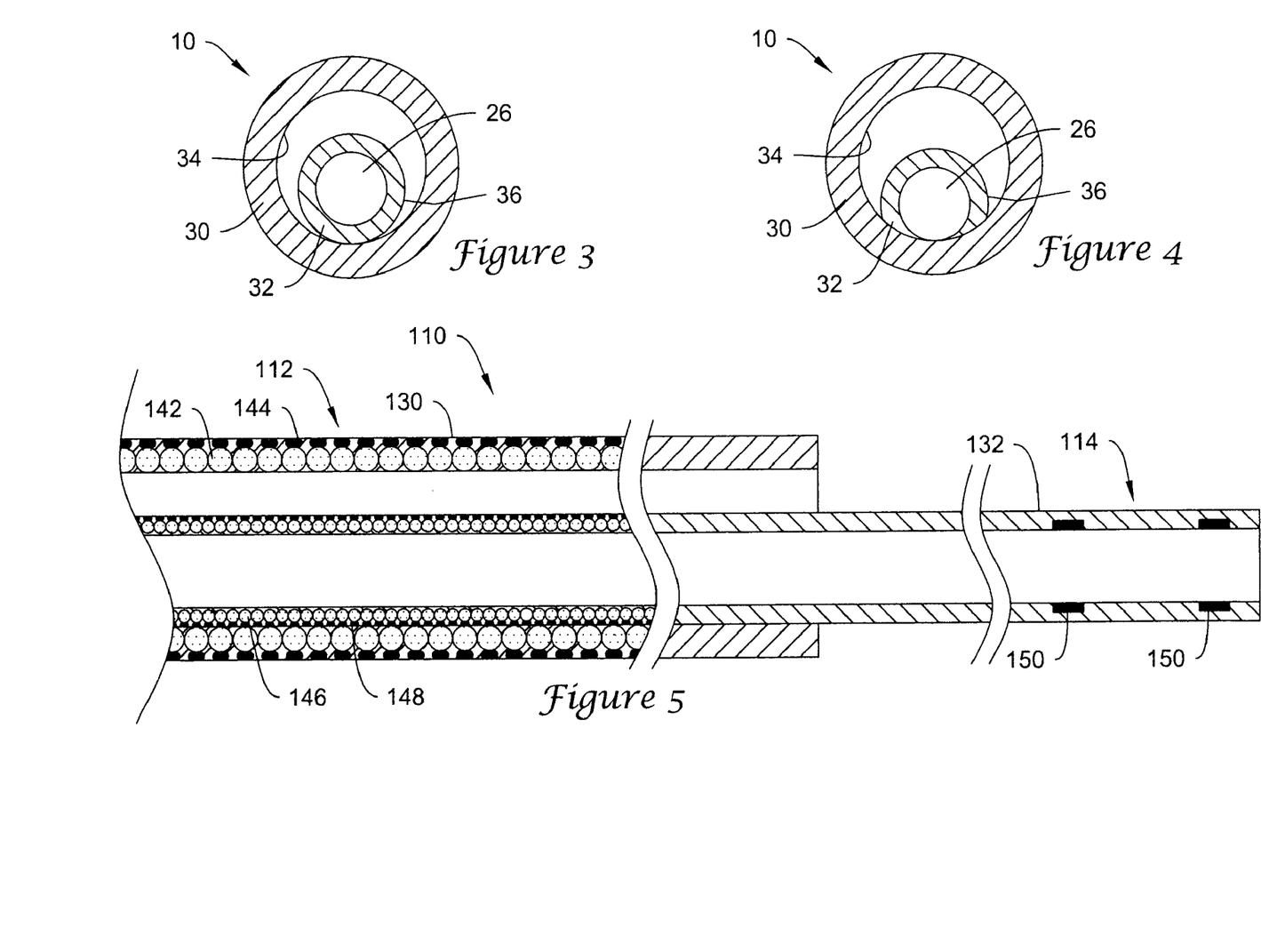
FIG. 3 is a cross-sectional view of the catheter shown in FIG. 2 taken through line 3-3.
FIG. 4 is an alternative cross-sectional view of the catheter shown in FIG. 1.
FIG. 5 is a cross-sectional view of another example catheter.

Tubular members 30/32 may be coupled to one another in a number of different manners. For example, FIG. 3 illustrates that tubular members 30/32 may be coupled by directly securing first tubular member 30 with second tubular member 32. For example, an outer surface 36 of tubular member 32 may be attached to an inner wall 34 of tubular member 30. The attachment may be manifested through the use of an adhesive, thermal bond, weld, mechanical connector, or any other suitable means. In alternative embodiments, tubular members 30/32 may have a different arrangement that may vary the manner in which they are bonded. For example, tubular member 32 could be coaxially disposed within tubular member 30, irregularly disposed within tubular member 30, include regions disposed in differing manner, disposed along the exterior of tubular member 30, and the like, or disposed in any other suitable arrangement.

Alternatively, tubular members 30/32 may be coupled during manufacturing via an extrusion process as seen in FIG. 4. According to this embodiment, catheter 10 (indicated in FIG. 4 as catheter 10') can be co-extruded so as to define "dual lumens" (i.e., lumens 16/26) along proximal region 12 and a single lumen (i.e., lumen 26) along distal region 14. The dual lumen proximal region 12 may define first tubular member 30 and second tubular member 32. The single lumen proximal region 14 would, therefore, define distance D of second tubular member 32 extending distally from proximal region 12. These alternative arrangements may entail alternative bonding strategies. In some embodiments, co-extrusion may take place in concert with the addition of other support structures (such as those seen in FIG. 5) or in the absence of such structures.

As suggested above, catheter 10 may take the form of a hybrid "micro guide" catheter. This nomenclature reflects the fact that catheter 10 may be a hybridization of some of the desirable characteristics and structure of typical microcatheters with some of the desirable characteristics and structure of typical guide catheters. For example, catheter 10 includes proximal region 12 that may have a proximal stiffness (similar to that of guide catheters) so as to provide a suitable level of pushability and torqueability when advancing catheter 10 through the vasculature. In addition, catheter 10 includes distal region 14 that can provide distal access to vascular targets and may have a distal flexibility (similar to that of microcatheters) suitable for navigating the tortuous vasculature. Distal region 14 can also serve as a guidewire or guiding structure over which other medical devices can be passed.

Because of the arrangement which second tubular member 32 extends distally from first tubular member 30, catheter 10 may be well suited for neurological applications. This is because the length (i.e., distance D) of tubular member 32 is typically long enough and suitably flexible so that it can navigate into the target neurological vasculature while proximal region 12 remains disposed in a more proximal location away from the head. Thus, the larger bore proximal region 12 can remain in larger vessels, while the smaller bore distal region 14 can advance through the smaller, more sensitive neuro-vasculature. Moreover, because first opening 40 of first tubular member 30 is set back distance D from second opening 38, contrast media can still be infused into the blood vessel (via lumen 16) that will travel within the blood stream toward the target site. Distance D may range from about 10 cm. to about 50 cm. For a preferred use in neurological applications, distance D is about 20 cm. to about 40 cm.

It should be noted that in addition to contrast media, a number of different substances may be passed through lumen 16. The substance may be generally described as a drug, chemotherapeutic, antibiotic, etc. Some examples of appropriate substances may include anti-thrombogenic agents and/or anticoagulants such as heparin, heparin derivatives, urokinase, and PPack (dextrophenylalanine proline arginine chloromethylketone) D-Phe-Pro-Arg chloromethyl keton, an RGD peptide-containing compound, antithrombin compounds, platelet receptor antagonists, anti-thrombin antibodies, anti-platelet receptor antibodies, aspirin, prostaglandin inhibitors, platelet inhibitors, and tick antiplatelet peptides; anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; anti-sense DNA and RNA; and DNA coding for (and the corresponding proteins) anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor a and β, platelet-derived endothelial growth factor, platelet-derived growth factor, tumor necrosis factor a, hepatocyte growth factor and insulin like growth factor, cell cycle inhibitors including CD inhibitors, thymidine kinase ("TK") and other agents useful for interfering with cell proliferation, and the family of bone morphogenic proteins ("BMP's") including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, BMP-16, "hedgehog" proteins.

FIG. 5 illustrates another example catheter 110. Catheter 110 is similar to catheter 10 except that first tubular member 130 and/or second tubular member 132 may include a variety of additional structural elements. For example, first tubular member 130 may include a coil 142, a braid 144, or multiples of either or both. Although coil 142 and braid 144 are depicted as being disposed at proximal region 112, this is not intended to be limiting as these structures could be disposed at essentially any position along first tubular member 130. Similarly, second tubular member 132 may also include a coil 146, a braid 148, or multiples of either or both. Again, the position of coil 146 and braid 148 may vary so as to be included at essentially any position along second tubular member 132.

Coils 142/146 and/or braids 144/148 may be similar to those typically seen in the art and can be made from any of the materials disclosed herein. Generally, coils 142/146 and/or braids 144/148 are provided as a reinforcing structure that can, for example, stiffen and/or strengthen the structure to which they are coupled. Because the distribution of support structures (i.e., coils 142/146, braids 144/148, etc.) can vary along the lengths of tubular members 130/132, regions having different flexibilities can be defined along catheter 110. Other structural modifications may also be present such as tapering of tubular members 130/132 in a regular, irregular, step-wise, or other manner. In some embodiments, coils 142/146 and/or braids 144/148 can be added subsequent an extrusion process or prior to an extrusion process (which would extrude another layer or material over coils 142/146 and/or braids 144/148). Of course, coils 142/146 and/or braids 144/148 are optional features that may be omitted from extrusion processes or other catheter manufacturing processes.

Coils 142/146 and/or braids 144/148 can also be used for other reasons including visualization. For example, coils 142/146 and/or braids 144/148 may be made from or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, plastic material loaded with a radiopaque filler, and the like. Likewise, other radiopaque structures may also be incorporated into catheter 10, such as marker bands 150.

Figure 6:
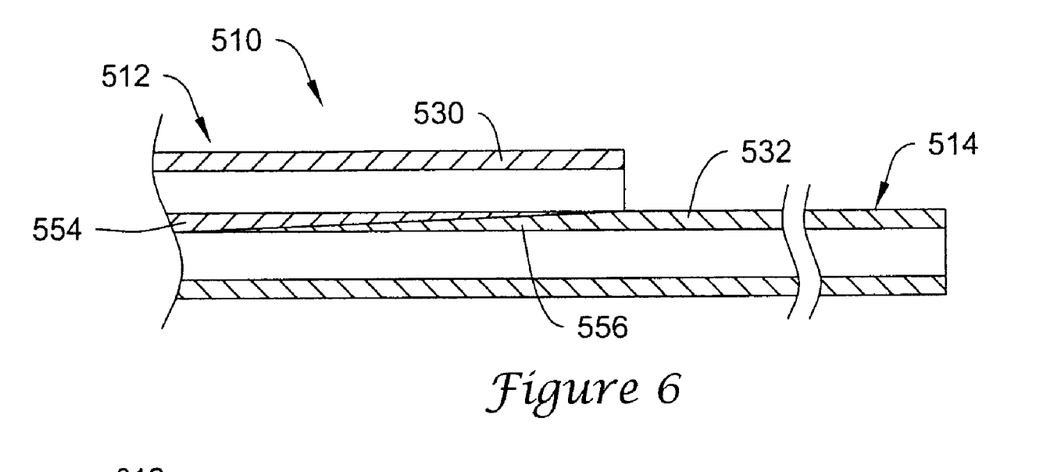
FIG. 6 is a cross-sectional view of another example catheter.

FIG. 6 illustrates another example catheter 510. Catheter 510 is similar to other catheters described herein except that first tubular member 530 and second tubular member 532 are arranged side-by-side and each include tapered regions. For example, first tubular member 530 may include tapered region 554 that tapers from "thick" to "thin" in the distal direction and second tubular member 532 may include tapered region 556 that tapers from "thin" to "thick" in the distal direction and mates with tapered region 554. This arrangement allows the flexibility characteristics of tubular member 530 to blend with those of tubular member 532. For example, tubular member 530 may be less flexible than tubular member 532 so that the overlapping tapered arrangement blends these flexibilities and creates a smooth transition in flexibility. Additionally, the overlapping arrangement may also allow for torque control or torqueability to be blended or otherwise progressively controlled.

The length, steepness or pitch, and position of tapered regions 554/556 may vary. For example, tapered regions 554/556 could extend along any portion (or all) of the length of catheter 510. In addition, any suitable steepness or abruptness in the amount of tapering can be utilized. Although overlapping tapered regions 554/556 are shown in FIG. 6 as being disposed at proximal portion 512, this feature is not intended to be limiting. For example, overlapping tapered regions 554/556 could be disposed at distal portion 514 or both proximal portion 512 and distal portion 514. Moreover, a number of additional overlapping tapered regions may be defined at essentially any position along catheter 510.

Figure 7:
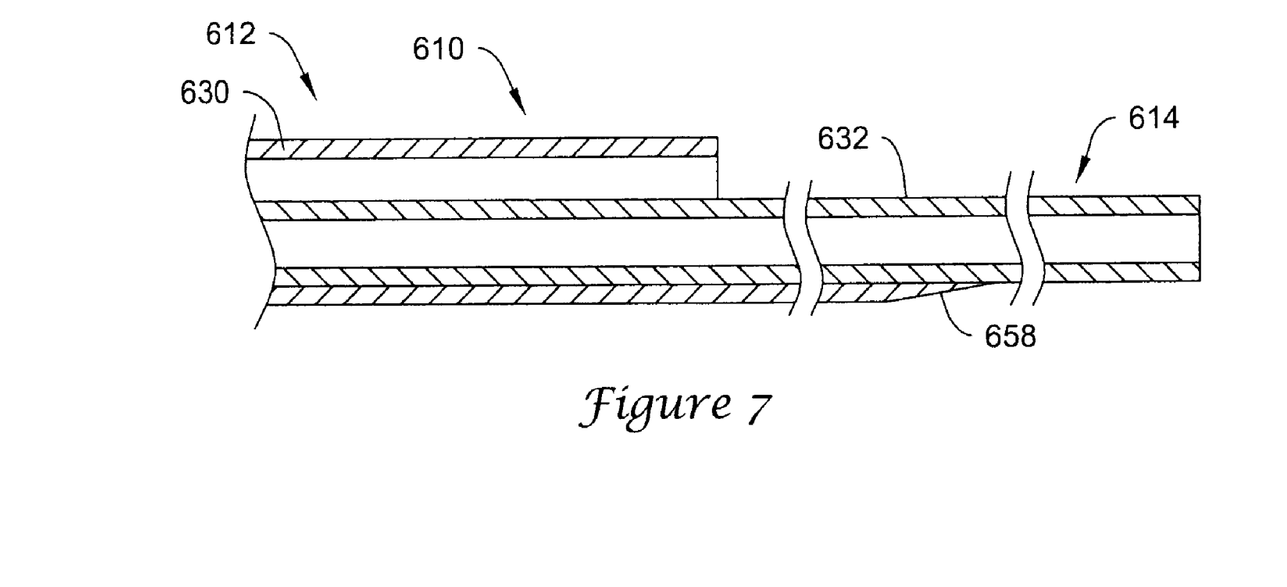
FIG. 7 is a cross-sectional view of another example catheter.

FIG. 7 illustrates another example catheter 610. Catheter 610 is similar to other catheters described herein except that only one tubular member, for example tubular member 630, includes a tapered region 658. Tapered region 658 may help blend the flexibilities of tubular members 630/632 as well add a number of other significant features as described above. Tapered region 658 may vary as described above in relation to tapered regions 554/556. For example, tapered region 658 may be disposed along proximal portion 612, distal portion 614, combinations thereof, or at any suitable location. Moreover, tapered region 658 could also be embodied by a taper defined in tubular member 632.

Figure 8:
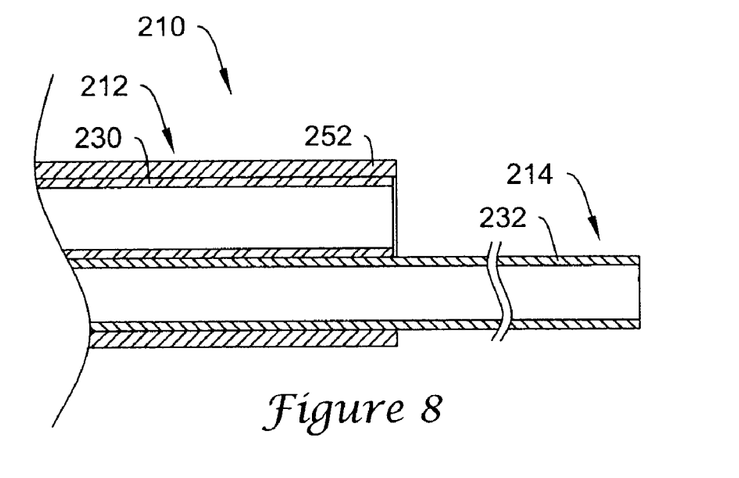
FIG. 8 is a cross-sectional view of another example catheter.

FIG. 8 illustrates another example catheter 210. Catheter 210 is similar to other catheters described herein except that first tubular member 230 and second tubular member 232 are disposed parallel to one another with first tubular member 230 being truncated relative to second tubular member 232. According to this embodiment, tubular members 230/232 can be secured together via any typical bonding technique (including those disclosed herein) or secured together with a mechanical connector such as a sheath 252. Generally, sheath 252 is disposed at proximal region 212 of catheter 210 and extends around at least a portion of both tubular members 230/232. The form and material composition of sheath 252 may vary. For example, sheath 252 may be made from a polymer such as those listed above. In a manner similar to the other disclosed embodiments, second tubular member 232 extends distally beyond first tubular member 230 to define distal region 214. The length of the distal region D can be selected as discussed above, especially for neurological applications.

Figure 9:
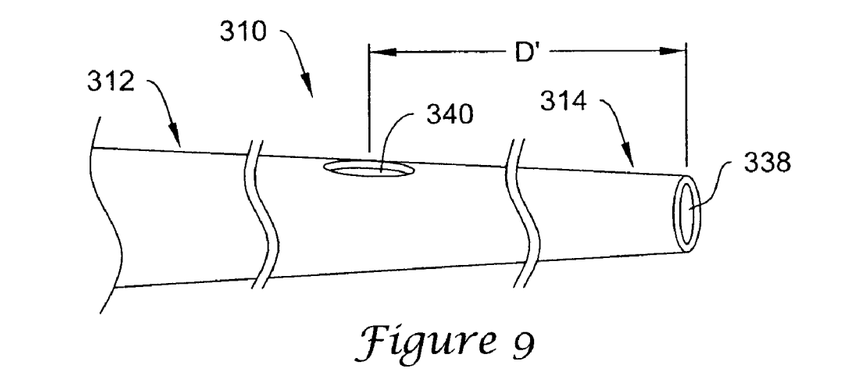
FIG. 9 is a side view of another example catheter.

FIG. 9 illustrates another example catheter 310. Catheter 310 includes proximal region 312 and distal region 314. The form of catheter 310 differs from the other catheters disclosed herein because rather than including multiple tubes, catheter 310 is generally formed of a singular, tapered tubular member. The taper defines variable outer diameter proximal and distal regions 312/314. Proximal region 312 may have an outer diameter suitable to impart the desired amount of stiffness. By virtue of being narrower, distal region 314 may impart the desired distal flexibility characteristics and distal access abilities described above. These and other features can be varied in a number of ways, such as by adding additional structures (such as coils and/or braids as seen in FIG. 3) to vary the flexibility. In some embodiments, distal region 314 may ultimately taper so that the inner diameter of distal region 314 corresponds to about the outer diameter of the microcatheter intended to extend therethrough. This feature can essentially "seal" catheter 310 so that contrast media can be essentially prevented from passing through opening 338. Alternatively, distal region 314 may remain slightly larger than the microcatheter so that fluid can pass through opening 338.

Similar to the other disclosed embodiments, catheter 310 includes first opening 340 and second opening 338 that are separated by a distance D'. Again, separating openings 340/338 by distance D' allows contrast media or other substances to be infused through catheter 310 and into the blood vessel through opening 340 and allows a microcatheter or other media device to be advanced through opening 338. This feature may be desirable, for example, in neurological applications where the vasculature may shift from relatively large vessels to small and/or sensitive vessels at or near the neurological treatment site.

Figure 10:
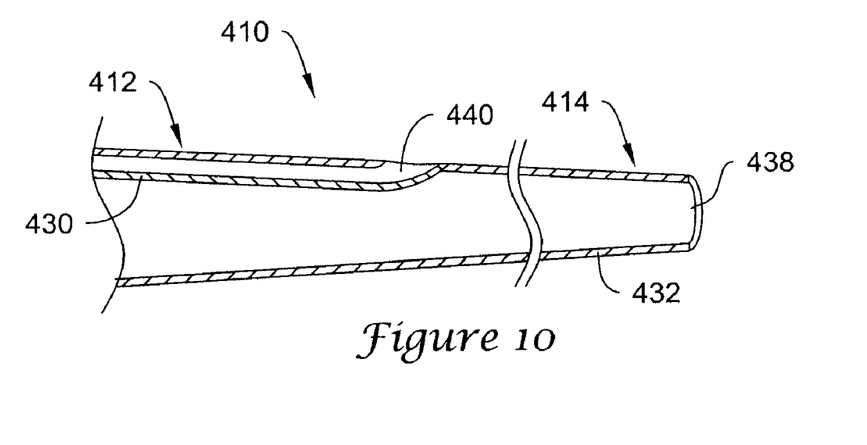
FIG. 10 is a cross-sectional view of another example catheter.

As described above, catheter 310 may be a singular tubular member. However, this need not be the case. For example, FIG. 10 illustrates another catheter 410 that is similar to catheter 310 except that it includes a first tubular member 430 and a second tubular member 432. According to this embodiment, proximal portion 412 may include both tubular members 430/432 similarly to some of the other embodiments described above. Tubular member 430 may terminate at opening 440 whereas tubular member 432 may terminate at opening 438 (which are separated a distance D' in essentially the same manner as shown in FIG. 9). This allows catheter 410 to function in a manner that is substantially similar to catheter 310.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A catheter, comprising:
    a first tube having a distal end and an outer surface;
    a second tube having a distal end and an outer surface; and
    wherein the first tube and the second tube are arranged in a side-by-side configuration;
    wherein the outer surface of the first tube includes a first region tapered in a first direction;
    wherein the outer surface of the second tube includes a second region tapered in a second direction different from the first direction;
    wherein the first region and the second region overlap and define a mated region;
    wherein the outer surface of the first tube is secured to the outer surface of the second tube along the mated region; and
    wherein the distal end of the first tube extends distally beyond the distal end of the second tube.

2. The catheter of claim 1, wherein the outer surface of the first tube is secured to the outer surface of the second tube with a thermal bond.

3. The catheter of claim 1, wherein the outer surface of the first tube is secured to the outer surface of the second tube with an adhesive bond.

4. The catheter of claim 1, wherein the outer surface of the first tube is secured to the outer surface of the second tube with a mechanical connector.

5. The catheter of claim 4, wherein the mechanical connector includes a sheath disposed about both the first tube and the second tube.

6. The catheter of claim 1, wherein the first tube, the second tube, or both have a plurality of slots formed therein.

7. The catheter of claim 1, wherein the first tube, the second tube, or both have a reinforcing coil disposed therein.

8. The catheter of claim 1, wherein the first tube, the second tube, or both have a reinforcing braid disposed therein.

9. The catheter of claim 1, wherein the first tube defines a catheter lumen, and further comprising a catheter disposed in the catheter lumen.

10. The catheter of claim 1, wherein the second tube defines a contrast media lumen, and further comprising contrast media disposed in the contrast media lumen.

11. The catheter of claim 1, wherein the distal end of the first tube extends 10 centimeters or more distally beyond the distal end of the second tube.

12. A catheter, comprising:
    a first tube having a distal end, an outer surface and a first portion;
    a second tube having a distal end, an outer surface and a second portion; and
    wherein the first tube and the second tube are arranged in a side-by-side configuration;
    wherein the first portion has a first wall thickness that thins in a distal direction;
    wherein the second portion has a second wall thickness that thins in a proximal direction; and
    wherein the first portion and the second portion are merged and define a merged wall having a constant wall thickness.

* * * * *